United States Patent
O'Hare et al.

(10) Patent No.: US 6,734,167 B2
(45) Date of Patent: May 11, 2004

(54) USES OF TRANSPORT PROTEINS

(75) Inventors: Peter Francis Joseph O'Hare, Surry (GB); Nadia Michelle Normand, Boulogne-Billancourt (FR); Neil Douglas Brewis, Surry (GB); Anne Phelan, Kent (GB)

(73) Assignee: Phogen Limited, Cambridge (GB)

( * ) Notice: Subject to any disclaimer, the term of this patent is extended or adjusted under 35 U.S.C. 154(b) by 0 days.

(21) Appl. No.: 09/747,772

(22) Filed: Dec. 20, 2000

(65) Prior Publication Data

US 2002/0155988 A1 Oct. 24, 2002

(51) Int. Cl.$^7$ .............................................. A61K 38/00
(52) U.S. Cl. ................... 514/12; 424/204.1; 424/231.1; 536/23.1; 536/23.5; 530/350
(58) Field of Search ........................ 514/12; 424/204.1, 424/231.1; 536/23.1, 23.5; 530/300, 350

(56) References Cited

U.S. PATENT DOCUMENTS 5,747,641 A    5/1998    Frankel et al.

FOREIGN PATENT DOCUMENTS

| WO | WO 97/05265 | 2/1997 |
|---|---|---|
| WO | WO 98/32866 | 7/1998 |
| WO | WO 98/42742 | 10/1998 |

OTHER PUBLICATIONS

Dalton et al, J. Clin. Oncol. vol. 7 p. 415 (1989).*

Fernandez et al. Nature Biotechnology vol. 16 p. 418 (1998).*

Murphy et al, Gene Therapy vol. 6 p. 4(1999).*

Orkin et al, report and Recommendations of the Panel to Assess the NIH Investment in Research on Gene Therapy (1995).*

Dilber et al.: "Intercellular delivery of thymidine kinase prodrug activating enzyme by the herpes simplex virus protein, VP22"—*Gene Therapy*, 6(1):12–21, 1999.

Elliott and O'Hare: "Intercellular Trafficking of VP22–GFP fusion proteins," *Gene Therapy*, 6, 149–151, 1999.

* cited by examiner

*Primary Examiner*—Sheela J. Huff
(74) *Attorney, Agent, or Firm*—Klarquist Sparkman, LLP

(57)     ABSTRACT

This invention relates to uses of transport-active proteins, particularly of proteins and fusion polypeptides with the function of VP22, for control of the cell cycle, particularly in the reduction of the proliferating activity of proliferating cells.

11 Claims, No Drawings

SEQUENCE LISTING

```
<160> NUMBER OF SEQ ID NOS: 5

<210> SEQ ID NO 1
<211> LENGTH: 66
<212> TYPE: DNA
<213> ORGANISM: synthetic construct

<400> SEQUENCE: 1
gatcctatgg ggcaggtggg acggcagctc gccatcatcg gggacgacat caaccgacgc     60
tatcgg                                                                66

<210> SEQ ID NO 2
<211> LENGTH: 65
<212> TYPE: DNA
<213> ORGANISM: synthetic construct

<400> SEQUENCE: 2
gatcccgata gcgtcggttg atgtcgtccc cgatgatggc gagctgccgt cccacctgcc     60
ccatg                                                                 65

<210> SEQ ID NO 3
<211> LENGTH: 20
<212> TYPE: DNA
<213> ORGANISM: synthetic construct

<400> SEQUENCE: 3
cccccaccac ttccctctc                                                   20

<210> SEQ ID NO 4
<211> LENGTH: 20
<212> TYPE: DNA
<213> ORGANISM: synthetic construct

<400> SEQUENCE: 4
cccccaccac ttccctctc                                                   20
```

```
<210> SEQ ID NO 5
<211> LENGTH: 36
<212> TYPE: RNA
<213> ORGANISM: synthetic construct

<400> SEQUENCE: 5
guuuucccug augaggccga aaggccgaaa uucucc                                     36
```

USES OF TRANSPORT PROTEINS

Applicants claim the benefit of the earlier filing date of Great Britain Application No. 9930519.5, filed Dec. 24, 1999, which is incorporated herein by reference in its entirety.

FIELD OF THE INVENTION

This invention relates to uses of transport-active proteins, particularly of proteins and fusion polypeptides with the function of VP22, for control of the cell cycle, particularly in the reduction of the proliferating activity of proliferating cells.

BACKGROUND OF THE INVENTION AND PRIOR ART

The transport properties of VP22 and homologues thereof are described in WO 97/05265 (P O'Hare and G Elliott). WO 98/32866 (P O'Hare et al.) discusses coupled polypeptides and fusion polypeptides for intracellular transport, and their preparation and use. Intercellular trafficking and protein delivery by a herpesvirus structural protein is described in Cell (1997), Vol. 88, pp223–233 (G Elliott and P O'Hare).

The prior art generally includes a variety of cell cycle control proteins, especially in the forms of protein and polynucleotide sequences enabling genetic manipulation by standard techniques.

For example, among cell cycle control proteins, protein p53 is known as a tumor suppressor. p53 is a 53 kDa nuclear phosphoprotein. Wild type and mutant p53 proteins have been expressed by means of recombinant vaccinia viruses (Ronen et al., Nucleic Acids Research, 20, pp 3435–3441, 1992). p53 functions to regulate cell cycle progression and under conditions of DNA damage can induce cell cycle arrest or apoptosis through a complex signal transduction mechanism (Levine A. J. Cell, 88, pp323–331, 1997).

Other proteins known to promote cell death include the bax protein, and homologues such as the Bak protein, including its BH3 domain (E P Hollinger et al., 1999, J Biol. Chem., 274 (19), pp 13298–13304).

SUMMARY AND DESCRIPTION OF THE INVENTION

According to an aspect of the invention there is provided a method of reducing cell proliferation, for example, a method of reducing proliferation of hyperproliferating cells, e.g. cancer cells, comprising the steps of:

a) exposing said proliferating cells, e.g. hyperproliferating cells, to a composition comprising at least one polypeptide comprising an amino acid sequence with the transport function of herpesviral VP22 protein, said polypeptide being coupled to at least one or a plurality of functionally active amino acid sequences, selected from proteins or peptides which can regulate cell cycle progression, e.g. proteins which can induce apoptosis, or proteins which can arrest cells from the cell cycle, for example at the G0 phase of the cell cycle, or functional analogues thereof; or exposing said cells to therapeutic compositions comprising nucleic acid encoding said protein(s) or nucleic acids which can regulate cell cycle progression; and b) exposing said cells to at least one agent to further stimulate cell death, said agent being selected from: drugs which can induce cell cycle arrest, cytotoxic chemotherapeutic drugs commonly used as part of a treatment of malignant disease, DNA damaging agents, agents which increase cellular sensitivity to DNA damage, and cytotoxic amounts of radiation; and optionally after step a) and/or step b)

c) further exposing said cells to at least one agent that can prevent export from the cell of any one of the agents administered in a) and/or b), for example, an Acf protein, or an inhibitor of the multi-drug resistance protein (MDR, also termed the P glycoprotein), e.g. an antisense molecule.

Proliferating cells which can be treated by the process of the invention can be tumor cells, for example tumor cells present in a tumor cell mass. Alternatively, the proliferating cells can be non-malignant cells, for example benign tumor cells such as genital warts, smooth muscle cells, such as vascular smooth muscle cells present in restenosis, or they can be proliferating skin cells, for example psoriasis or eczema skin cells, or proliferating cells of scar tissue.

Among the VP22 coupled proteins useful in step a) of the method can be fusion proteins, or if desired they can be chemically coupled proteins comprising a VP22 protein and a cell cycle regulatory protein. Nucleic acids useful in step a) of the method can be nucleic acids encoding VP22 fusion proteins.

Proteins which can be coupled to VP22 and which can usefully regulate cell cycle progression according to a method of the invention include, for example, inhibitors of cyclin-dependent kinases (CKIs). Suitable such inhibitors include proteins which can arrest cells at the G1/S or G2/M cell boundaries of the cell cycle, e.g. proteins p27-kip1, p21-waf1/cip1, p15-ink4b, p16-ink4a, p57-kip2 and p19-ARF. p27 is described for example by K Polyak et al. in Cell (1994), 78, pp 59–66, and by J. A. Pietenpol et al. in Cancer Research (1995), 55 (6), pp 1206–1210.

Thus an aspect of the invention includes a pharmaceutical preparation of a coupling product between a protein with the transport function of VP22 and a protein with the function of regulating cell cycle progression, e.g. by inducing cell apoptosis or arresting cells from the cell cycle. A further aspect of the invention comprises the use of the preparation for contacting proliferative cells to reduce their proliferative activity.

Other proteins which can usefully be coupled to VP22 according to further embodiments of the invention and which can regulate cell cycle progression can be, for example, proteins which under conditions of DNA damage induce cell apoptosis, e.g. p53, or proteins which under conditions of DNA damage arrest cell growth, e.g. a protein product of the GADD gene family, e.g. the product of GADD45 or GADD 153.

WO 98/32866 (Marie Curie Cancer Care: P 'O Hare et al.) further describes proteins which can usefully be coupled to VP22, e.g. p53, and also vectors expressing such coupled polypeptides.

Further examples of proteins which can be coupled to VP22 and which can induce cell apoptosis include the following: cytochrome c, members of the caspase protease family of proteins, the apoptin protein, the bak protein and also the bax protein, and any homologues or functional fragments thereof, particularly the functional 19 amino acid domain of the bak and bax proteins, termed the BH3 domain, and functional homologues thereof.

Amounts of VP22 coupled to a cell cycle regulatory protein (or encoding polynucleotide) which can be usefully administered to a patient in a method according to the invention range from about 0.001 micrograms per kg (weight of a subject to be treated) to about 100 milligrams per kg.

Examples of drugs which can be used to induce cell cycle arrest in examples of methods of the invention include flavopiridol, taxol and nocodazole. Doses of taxol which can be administered in a method of the invention can be for example, about 135 to about 175 milligrams per sq.m. (body area of a subject to be treated), and can be given as an infusion through an in-line filter over a time period of hours, e.g. 24 h. Taxol can be used in combination with cisplatin (cisdiamminedichloroplatinum), which can be given at a dosage of, e.g. 70–80 mg per sq.m., after administration of taxol. Combination treatment with taxol followed by cisplatin is especially useful as part of a therapy for ovarian carcinoma.

Chemotherapeutic drugs which can be used to treat proliferating cells in examples of methods of the invention, can be for example, doxorubicin, etoposide, phelomycin D, paclitaxel, curcumin, or camptothecin. Standard dosages of chemotherapeutic drugs can usefully be given to a patient to be treated. For example, for doxorubicin dosage is usually calculated on the basis of body area, and doses which can usefully be administered as part of the method of the invention are 60–70 mg per sq.m., e.g. 30–40 mg per sq.m., this can be administered as a single dose, by for example intravenous administration, e.g. every three weeks.

DNA damaging agents which can be used to treat proliferating cells in examples of methods of the invention can be for example, DNA chelating agents, such as cisplatin. This can be given by infusion over a period of hours, e.g. in doses upwards of 20 mg per sq.m. (body area of a subject to be treated), e.g. 60–70 mg per sq.m., e.g. 30–40 mg per sq.m., administered, for example, every three weeks.

Agents which can sensitize a cell to DNA damage in examples of methods of the invention include for example, inhibitors of proteins which export DNA damaging agents from cells, e.g. inhibitors of P glycoprotein (MDR protein), e.g. MDR antisense; and also inhibitors of proteins which are involved in recognition of DNA damage, e.g. inhibitors of proteins selected from: poly ADP ribose polymerase (PARP), ataxia-telangiectasia (ATM) and DNA protein kinase.

Use of a DNA damaging agent, for example cisplatin, to treat proliferating cells in examples of methods of the invention is particularly preferred when said proliferating cells are to be exposed to VP22 coupled to a protein which under conditions of DNA damage induces cell apoptosis, for example p53.

When proliferating cells are exposed to p53 it can also be particularly useful to further expose the cells to the ARF protein, which prevents export from the cell and subsequent degradation of p53, or to a nucleic acid encoding the ARF protein.

When proliferating cells are exposed to a chemotherapeutic drug according to an example of a method of the invention it can also be particularly useful to further expose said cells to an agent which can prevent export of the chemotherapeutic drug from the cell, for example, an inhibitor of the multi-drug resistance protein (MDR), e.g. an antisense molecule of the MDR protein.

According to an aspect of the invention, the VP22 coupled polypeptides described herein, or the corresponding encoding polynucleotides can be delivered to proliferating cells, by for example, direct injection into target cells, such as a tumor cell mass, or they can be delivered systemically.

The compositions can also be formulated using per se known methods for topical delivery, e.g. to treat psoriasis, eczema or skin cancer. Alternatively, they can be encapsulated into slow release capsules suitable for oral delivery using methods known in the art.

The VP22 coupled polypeptides or the corresponding encoding polynucleotides can also be associated with other delivery systems, for example they can be coupled to liposomes, such as cationic liposomes, or they can be associated with condensing agents, such as DNA condensing agents, e.g. hydrophilic polymers, e.g. protamine sulphate, or e.g. lysine. They can then be delivered by e.g. direct injection into the target cells, such as tumor cells, or alternatively they can be delivered systemically, e.g. using a catheter based approach, or they can be formulated for topical delivery or oral delivery.

To enhance delivery to target cells the therapeutic compositions described herein can also usefully comprise a targeting molecule, e.g. a tumor targeting molecule, such as transferrin or folate. The targeting molecule can be, for example, coupled, e.g. by fusion, to VP22.

Alternatively, according to a further aspect of the invention hyperproliferative cells can be exposed to VP22 fusion polypeptides described herein by introducing an expression vector encoding said fusion polypeptide into the target population of said proliferating cells, e.g. by direct injection into the target site. The expression vector can be for example, a recombinant virus vector, such as an adenovirus vector, an adeno-associated virus, or a herpesvirus vector. Particularly useful in this context are defective herpesvirus vectors such as those described in specifications: WO 92/05263 (Immunology Ltd: Inglis et al.), WO 96/26267 (Cantab Pharmaceuticals Research Ltd: Inglis et al.) and WO 96/04395 (Lynxvale Ltd: Speck) and documents cited therein. When the vector is a herpesvirus it can be useful to deliver from $1 \times 10^3$ to $1 \times 10^8$ pfu of virus, e.g. from $1 \times 10^4$ to $1 \times 10^7$ pfu. When the vector is an adenovirus or an adeno-associated virus it can be useful to deliver from $1 \times 10^3$ to $1 \times 10^{13}$ pfu of virus.

According to another aspect of the invention the hyperproliferative cells can be exposed to VP22 coupled polypeptides described herein by introducing into said cells aggregated compositions comprising VP22 protein non-covalently associated with oligonucleotides or polynucleotides. Such non-covalently associated compositions can be produced by mixing oligo- or polynucleotides with VP22 protein at preferred ratios, e.g. of between 2:1 and 1:1 of protein to nucleotide. Oligo- or polynucleotides suitable for forming part of the aggregates can preferably comprise at least about 10 bases and in length and can vary widely in size, they can be about 10 kilobases in size, or e.g. about 10–100 bases in size, e.g. about 20 bases. The oligo- or polynucleotide can encode a protein or peptide which it is desired to introduce into the cell, for example, a cell cycle control protein. Alternatively, the oligo- or polynucleotide can be antisense, e.g. antisense to a protein which inhibits apoptosis, such as the Bcl protein, or the oligo- or polynucleotide can have the function of correcting splicing defects. The oligo- or polynucleotides can also usefully be chimeroplasts which can correct mutations, or they can be molecules which can form triple helices and function to down-regulate gene expression. The oligo- or polynucleotides can also be ribozymes which can be used to inhibit target gene expression, for example they can be the synthetic hammerhead ribozyme, or functional homologues or modifications thereof, which can recognize and cleave c-myb RNA, thereby inhibiting cell proliferation (Jarvis et al., J. Biol. Chem., 1996, 271, 29107–29112).

When VP22 coupled polypeptides are delivered to proliferating cells by introducing into said cells said aggregated compositions of VP22 protein and oligonucleotides or polynucleotides, the aggregated composition can optionally further comprise a photosensitizing molecule, e.g. fluoroscein, rhodamine, or TRITC, which can be linked to the 5' or 3' end of the synthetic nucleotide. This can facilitate the dissociation of the aggregate in the presence of irradiation, e.g. during phototherapy, for example, as part of a treatment for skin cancer or psoriasis. It can be especially preferred to use the dye BODIPY -630/650 (from Molecular Probes, Oregon, USA) as the photosensitizing molecule during phototherapy since it absorbs light of a higher wavelength, e.g. about 630 nm and this penetrates body tissues better than light of lower wavelength. Irradiation can be achieved, for example, by introducing into a patient to be treated an endoscope comprising laser optic lines for emitting radiation. Dissociation of aggregates can also be facilitated in the absence of light by introduction of a cleavage site, such as a protease site, or a fusogenic peptide, e.g. the FLU fusion peptide.

Other examples of useful molecules which can promote disassociation of aggregates in the presence of irradiation, e.g. during phototherapy, include phthalocyanine-containing chromophores, for example aluminum or zinc phthalocyanine. Such molecules can be administered as part of a composition with the aggregates, or they can be administered separately not forming part of the composition, e.g. by direct injection at the same locus as the aggregates or at a closely neighboring locus. It can be especially useful to administer aluminum phthalocyanine to promote disassociation of aggregates when the proliferating cells are tumor cells, since aluminum phthalocyanine is known to be preferentially absorbed by tumor cells. Aluminum phthalocyanine can promote disassociation of aggregates by irradiation with light of a wavelength of about 675 nm.

Alternatively, molecules can be used which can promote disassociation of aggregates in the absence of light, for example chloroquine and tamoxifen. It can be particularly useful to administer tamoxifen when the proliferating cells are cancer cells, e.g. breast cancer cells. The agents can usefully be administered as part of a composition with the aggregates, or separately not forming part of the composition, e.g. by direct injection at the same locus as the aggregates or at a closely neighboring locus.

Hyperproliferative cells can be exposed to an agent according to step b) or step c) of the method of the invention by either administration of said agent alone, or alternatively by introducing said agent coupled to an amino acid sequence with the transport function of VP22 protein. Where said agent is a polypeptide or protein it can be useful to deliver the encoding polynucleotide, e.g. as an aggregated composition. Said agents can be delivered to target cells using delivery methods previously described, for example, by systemic delivery, topical delivery, or by direct injection into said target cells, or alternatively by use of delivery systems, such as liposomes.

The therapeutic composition comprising VP22 protein or encoding nucleic acid can be coupled or fused to more than one non-VP22 protein or nucleic acid, to form a multivalent composition.

Multivalent compositions which can be particularly useful to induce cell apoptosis are compositions comprising VP22 and bax or Bak and cytochrome c proteins, or functionally equivalent homologues or fragments of these proteins, particularly for example, the functional 19 amino acid domain of the bax protein, termed the BH3 domain or functional homologues thereof, or encoding nucleic acids. Also particularly useful are compositions comprising VP22 and p53 and acf proteins, or functionally equivalent homologues or fragments of these proteins, or encoding nucleic acids.

Other examples of useful multivalent compositions are compositions comprising VP22 coupled to more than one cell cycle control protein or encoding nucleic acid, for example, to proteins which induce apoptosis or which arrest cells from the cell cycle, e.g. at the G0 stage of the cell cycle, for example by coupling VP22 to more than one protein or functionally active peptide fragment or encoding nucleic acid selected from: p27-kip1, p21-waf1/cip1, p15-ink4b, p16-ink4a, p57-kip2 and p19-ARF, p53, p18-ink4c. Examples of especially preferred fusions are: a fusion comprising VP22 protein and p53 and p21-kip1 and/or p19-ARF proteins, or encoding nucleic acids; and also a fusion comprising VP22 and p53 and p16-ink4a and/or p27-kip1, or encoding nucleic acids.

It can also be useful to couple VP22 to one or more cell cycle control proteins and additionally to other proteins or peptides, such as proteins or peptides which can function as cell targeting molecules, e.g. which interact with receptors on surface of malignant cells. For example, it can be useful to couple VP22 to the folate or transferrin protein.

In another aspect of the invention, said multivalent compositions can comprise aggregated compositions of non-covalently associated VP22 protein and oligonucleotides or polynucleotides, wherein more than one oligo- or polynucleotide is present. Optionally, VP22 protein can be present in said aggregates as a coupled or fusion protein, e.g. as a multivalent VP22 fusion protein.

A composition which can be usefully administered in step a) of the method of the invention is a fusion protein comprising VP22 coupled to the BH3 domain of the bak protein, which is a functional homologue of the BH3 domain from the bax protein (E P Hollinger et al., 1999, J. Biol. Chem., 274 (19), pp13298–13304) and can be made as follows:

The '159–301' VP22 protein which consists of amino acids 159–301 of VP22 can be made in an *E.coli* pET expression system from a plasmid expressing amino acids 159–301 of VP22 under control of an IPTG sensitive promoter. If a his tag is desired for purification purposes, then it is preferably placed at the C terminus of the protein.

A double stranded oligonucleotide with the following sequence corresponding to BH3 can be made and cloned into the Bam H1 site of the '159–301' VP22 protein expression plasmid as mentioned above using techniques known in the art:

```
                                          (SEQ ID NO: 1)
5'GATCCTATGGGGCAGGTGGGACGGCAGCTCGCCATCATCGGGGA

CGACATCAACCGACGCTATCGG (SEQ ID NO: 2)
5'GATCCCGATAGCGTCGGTTGATGTCGTCCCCGATGATGGCGAGC

TGCCGTCCCACCTGCCCCATG
```

The above strands are complementary such that the sequence of the first strand from the seventh residue (adenine) in the 5' to 3' direction is complementary with the sequence of the second strand from the second residue from the end (thymine) in the 3' to 5' direction.

BL21 *E. coli* cells can be transformed with this BH3-'159–301' VP22 protein expression plasmid, and a single colony transformant used to inoculate 3.2L of a suitable nutrient broth, such as L nutrient broth (Oxoid) and which also contains Kanamycin.

The recombinant bacteria expressing BH3-'159–301' VP22 protein can be induced by addition of IPTG (1 mM) to a logarithmic phase culture, and the pellets harvested by centrifugation (6000 rpm, 4 deg C., 20 min). After pelleting the cells can be resuspended in 40 ml of cold lysis buffer containing: 50 mM sodium phosphate (pH 8.0), 300 mM sodium chloride, 5 mM imidazole (pH 8.0), 5 mM beta-mercaptoethanol, 1 microg/ml of leupeptin, 1 microg/ml pepstatin and 1 mg/ml lysozyme.

The lysis mixture is incubated for 30 min with occasional shaking, and is then sonicated on ice three times for 15 seconds followed by addition of 0.1 NP-40. Dnase and Rnase are then added to 10 microg/ml and incubated on ice for 20 min with occasional shaking. The lysate is then drawn through a narrow gauge syringe three times. This is followed by centrifugation of the lysate at 20,000 rpm for 15 min at 4 deg C. The supernatant containing the VP22-BH3 fusion protein is retained. The BH3-'159–301' VP22 fusion protein can be purified as follows:

The protein can be enriched by ion exchange chromatography on DEAE sepharose (Pharmacia) by using a batch method, in the presence of lysis buffer comprising 50 mM sodium phosphate (pH 8.0), 300 mM sodium chloride, 5 mM imidazole (pH 8.0), 5 mM beta-mercaptoethanol, 0.1% NP-40, and 1 microgram/ml leupeptin and 1 microgram/ml pepstatin.

The eluate is then further purified on nickel-NTA beads in a batch method. Protein is bound to the beads at 4 deg C. for 1 h. The beads are then washed three times for 30 mins in wash buffer, which has the same composition as lysis buffer except that it contains 10% glycerol, 0.1% NP-40, 40 mM imidazole (pH 8.0). Bound protein is then eluted three times in 1 ml of eluate buffer each time. The eluate buffer has the same composition as lysis buffer except that it contains 10% glycerol, 0.1% NP-40, 500 mM imidazole (pH 8.0). The eluate buffer can then be exchanged by PD-10 sephadex column chromatography into PBS, 10% glycerol, 5 mM B-mercaptoethanol.

The BH3-'159–301'VP22 fusion protein can then be used in the preparation of a sterile pharmaceutical formulation suitable for administration to a patient and prepared by formulating the BH3-'159–301'VP22 fusion protein with pharmaceutically acceptable carrier material. The sterile pharmaceutical formulation can than be administered to a patient, for example, by direct injection into a tumor cell mass.

Alternatively, the BH3-'159–301' VP22 fusion protein can be stored in PBS at −70 deg C., or it can be lyophilized prior to storage at −70 deg C., and re-constituted prior to use.

The BH3-'159–301' VP22 fusion protein obtained by the method described above can also be used in the formation of aggregated compositions comprising non-covalently associated BH3-'159–301' VP22 and oligo or poly-nucleotides. Such a composition can be made as follows:

22.5 microliters of BH3-'159–301' VP22 protein in PBS is added to 2.5 microliters of PBS and 0.5 microliters of a FITC labelled 20 mer oligonucleotide (which happens to be a conveniently available base sequence complementary to a segment of mRNA encoding the intracellular-adhesion molecule, or ICAM) with a sequence as follows:

5'CCC CCA CCA CTT CCC CTC TC 3' (SEQ ID NO: 3), and labeled at the 5'end with FITC The final concentration of BH3-'159–301' VP22 fusion protein is 18 micrograms per ml and the final concentration of oligonucleotide is 500 nM. The mixture is then mixed and left at room temperature for at least 10 minutes. It can then be used in the preparation of a sterile pharmaceutical formulation suitable for administration to a patient and prepared by formulating with pharmaceutically acceptable carrier material. The sterile pharmaceutical formulation can than be administered to a patient, for example, by direct injection into a tumor cell mass.

Prior to, concurrently, or after administration of the BH3-'159–301' VP22 protein, the patient can also be given an infusion of an agent to further stimulate cell cycle arrest or cell apoptosis, for example taxol, e.g. 175 mg per $m^2$ given through an in-line filter over a period of 24 h.

When the BH3-'159–301' VP22 protein is administered as an aggregated composition as described above it can be particularly useful to further subject the patient to photodynamic therapy after administration of the aggregated composition. This can be achieved, for example, by introducing into a patient an endoscope comprising laser optic lines for local irradiation, and which emits light in the range of about 350–850 nm, in the region of the site of injection of the aggregates.

A p27-'159–301' VP22 fusion protein can be made in a method analogous to that described for making a BH3-'159–301' VP22 fusion protein, except that an oligonucleotide with a sequence corresponding to the p27 sequence (GenBank Accession Number U10906) is made and cloned into the Nde I and Bam Hl sites of the '159–301' VP22 expression plasmid.

The p27-'159–301' VP22 fusion protein can then be used in the preparation of a sterile pharmaceutical formulation suitable for administration to a patient and prepared by formulating the p27-'159–301' VP22 fusion protein with pharmaceutically acceptable carrier material. The sterile pharmaceutical formulation can than be administered to a patient, for example, by direct injection into a tumor cell mass.

Alternatively, the p27-'159–301' VP22 fusion protein can be stored in PBS at −70 deg C., or it can be lyophilized prior to storage at −70 deg C., and re-constituted prior to use.

The p27-'159–301' VP22 fusion protein obtained by the method described above can also be used in the formation of aggregated compositions comprising non-covalently associated p27-'159–301' VP22 and oligo or poly-nucleotides. Such a composition can be made as follows:

37 microliters of p27-'159–301' VP22 protein in PBS is added to 463 microliters of PBS and 5 microliters of a FITC labeled ICAM 20 mer oligonucleotide with a sequence as follows:

5'CCC CCA CCA CTT CCC CTC TC 3' (SEQ ID NO: 4)

The final concentration of p27-'159–301' VP22 fusion protein is 185 micrograms per milliliter and the final concentration of oligonucleotide is 2.5 micromolar. The mixture is then mixed and left at room temperature for at least 10 minutes. It can then be used in the preparation of a sterile pharmaceutical formulation suitable for administration to a patient and prepared by formulating with pharmaceutically acceptable carrier material. The sterile pharmaceutical formulation can than be administered to a patient, for example, by direct injection into a tumor cell mass.

Prior to, concurrently, or after administration of the p27-'159–301' VP22 protein, the patient can also be given an infusion of, an agent to further stimulate cell cycle arrest or cell apoptosis, for example taxol, e.g. 175 mg per $m^2$ given through an in-line filter over a period of 24 h.

This example concerns preparation of an aggregated composition comprising (i) a fragment of VP22, herein designated VP22 159–301 protein (ii) and an oligonucleotide which is a 36 mer ribozyme as described by Jarvis et al., J. Biol. Chem. 1996, 271, 29107–29112, which can recognize and cleave c-myb and so inhibit cell proliferation, and which is fluorescein labeled at the 5' end and has the following sequence and can be obtained from Cruachem, Glasgow, UK:

(SEQ ID NO: 5)
5'GUUUUCCCUGAU GAGGCCGAAAGGCCGAAAUUCUCC 3', all nucleotides are 2'-0-methyl nucleotides with the exception of the following: U at position U5 (i.e. the fifth U residue counting from the 5' end of the sequence), G at positions G2, G3 and G9, A at positions A1 and A8 are 2' hydroxyl (ribo)nucleotides. The U at position U5 indicates 2'-0-allyl uridine, the ribozyme described by Jarvis et al. Had a 2'-C-allyl uridine linkage at this position (this being the only difference between the ribozyme described here and that of Jarvis et al.). 5-phosphorothioate linkages are present at the 5' and 3' ends, other linkages are phosphodiester.

Aggregates can be produced by adding the 36 mer oligonucleotide to the 159–301 protein solution in PBS as previously described in example 1 so that the final concentrations in 50 microliters of solution are: 18 micrograms per ml (or alternatively 32 micrograms per ml) protein and 500 nM oligonucleotide.

The formation of the aggregates of the invention can be monitored by using microscopy e.g. phase contrast or fluorescence microscopy, or by agarose gel electrophoresis of the aggregates.

The aggregated composition produced can then be used as previously mentioned in the preparation of a sterile pharmaceutical formulation which can be administered to a patient, for example, by direct injection into a tumor cell mass.

The present invention and disclosure extends to the methods and compositions and the resulting products as described herein, and to modifications and variations of the steps and features mentioned in the present description, including all combinations and subcombinations of the steps and features hereof, including variations in the order and selection of the steps, and the documents cited herein are hereby incorporated by reference in their entirety for all purposes.

What is claimed is:

1. A method of reducing proliferation of cells comprising:
   (a) exposing said cells to a composition comprising at least one polypeptide comprising an amino acid sequence with the transport function of herpesviral VP22 protein, said polypeptide being coupled to at least one functionally active acid sequence, wherein the functionally active amino acid sequence is a protein or peptide which can regulate cell cycle progression, or functional analogue thereof; and
   (b) exposing said cells to at least one agent to further stimulate cell death, said agent selected from: drugs which can induce cell cycle arrest, cytotoxic chemotherapeutic drugs used as part of a treatment program of malignant disease, DNA damaging agents, agents which increase cellular sensitivity to DNA damage, and cytotoxic amounts of radiation.

2. A method according to claim 1, wherein said cells are hyperproliferating cells.

3. A method according to claim 1, wherein said coupled polypeptide can induce apoptosis, or can arrest cells from the cell cycle.

4. A method according to claim 2, wherein said cells are cancer cells.

5. A method according to claim 3, wherein said polypeptide is a cyclin-dependent kinase inhibitor.

6. A method of reducing proliferation of cells comprising exposing said cells to a preparation comprising:
   (a) a coupling product between a protein with the transport function of VP22 and a protein which can regulate cell cycle progression, and
   (b) at least one agent to further stimulate cell death, said agent being selected from the group consisting of: drugs which can induce cell cycle arrest, cytotoxic chemotherapeutic drugs used as part of a treatment programme of malignant disease, DNA damaging agents, and agents which increase cellular sensitivity to DNA damage, in combination with a suitable pharmaceutical excipient, thereby reducing proliferation of said cells.

7. A method according to claim 1, wherein the polypeptide is coupled to a plurality of functionally active amino acid sequences.

8. A method according to claim 1, comprising further (c) exposing said cells to at least one agent that can prevent export from the cell of any one of the agents administered in a) and/or b), wherein said exposure occurs after step a) and/or step b).

9. A method according to claim 8, wherein said agent that can prevent export from the cell of any one of the agents administered in a) and or in b) is an inhibitor of the multi-drug resistance protein.

10. A method according to claim 9, wherein said agent is an anitsense molecule.

11. The method of claim 6, and wherein said preparation further comprises (c) at least one agent that can prevent export from the cell of at least one of the agents (a) or (b).

* * * * *

UNITED STATES PATENT AND TRADEMARK OFFICE
CERTIFICATE OF CORRECTION

| | | |
|---|---|---|
| PATENT NO. | : 6,734,167 B2 | Page 1 of 1 |
| APPLICATION NO. | : 09/747772 | |
| DATED | : May 11, 2004 | |
| INVENTOR(S) | : O'Hare et al. | |

It is certified that error appears in the above-identified patent and that said Letters Patent is hereby corrected as shown below:

In the Claims:

Column 12, line 35, claim 9, "a) and or in b)" should read --a) and/or in b)--.

Column 12, line 38, claim 10, "anitsense" should read --antisense--.

Signed and Sealed this

Twenty-second Day of May, 2007

JON W. DUDAS
*Director of the United States Patent and Trademark Office*